(12) United States Patent
Paul et al.

(10) Patent No.: US 8,097,757 B2
(45) Date of Patent: Jan. 17, 2012

(54) METHOD FOR PREPARING (METH)ACRYLIC ANHYDRIDE

(75) Inventors: Jean-Michel Paul, Metz (FR); Serge Tretjak, Roulhing (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/863,033

(22) PCT Filed: Jan. 27, 2009

(86) PCT No.: PCT/FR2009/050113
§ 371 (c)(1),
(2), (4) Date: Aug. 11, 2010

(87) PCT Pub. No.: WO2009/098422
PCT Pub. Date: Aug. 13, 2009

(65) Prior Publication Data
US 2010/0317892 A1  Dec. 16, 2010

(30) Foreign Application Priority Data
Feb. 8, 2008 (FR) ..................... 08 50802

(51) Int. Cl.
*C07C 51/56* (2006.01)
*C07C 53/00* (2006.01)

(52) U.S. Cl. .................. 562/895; 562/887
(58) Field of Classification Search .............. None
See application file for complete search history.

(56) References Cited

U.S. PATENT DOCUMENTS

| | | | |
|---|---|---|---|
| 4,857,239 A * | 8/1989 | Hurtel et al. | 562/896 |
| 7,074,957 B2 | 7/2006 | Dupont et al. | |
| 2002/0161260 A1 | 10/2002 | Schmitt et al. | |
| 2003/0018217 A1* | 1/2003 | Dupont et al. | 562/888 |
| 2008/0161596 A1 | 7/2008 | Riondel et al. | |
| 2009/0234161 A1 | 9/2009 | Paul | |
| 2009/0264673 A1 | 10/2009 | Broell et al. | |
| 2010/0069666 A1* | 3/2010 | Broell | 562/888 |

* cited by examiner

*Primary Examiner* — Karl J Puttlitz
(74) *Attorney, Agent, or Firm* — Kimberly R. Hild

(57) ABSTRACT

The present invention relates to an improved method for preparing (meth)acrylic anhydride ($A(M)A_2O$) by transanhydrification between (meth)acrylic acid and acetic anhydride in the presence of at least one polymerization inhibitor, in which reaction to the point of partial conversion of the reagents is carried out, followed by continuous distillation. With the method according to the invention, it is possible to produce $I1A(M)A_2O$ of very high purity under improved productivity conditions compared to existing methods while eliminating problems of reactor fouling.

8 Claims, 1 Drawing Sheet

METHOD FOR PREPARING (METH)ACRYLIC ANHYDRIDE

FIELD OF THE INVENTION

The present invention relates to an improved process for the manufacture of (meth)acrylic anhydride by transanhydrization between (meth)acrylic acid and acetic anhydride, in which the reaction is carried out until the reactants have been partially converted, followed by continuous distillation.

The term "(meth)acrylic anhydride", which will subsequently be denoted by $(M)AA_2O$, is understood to mean methacrylic anhydride and acrylic anhydride.

BACKGROUND OF THE INVENTION

It has been known for a long time, for example from Application EP 231 689, that it is possible to prepare (meth)acrylic anhydride by reaction of acetic anhydride with (meth)acrylic acid in the presence of polymerization inhibitors. The acetic acid formed is distilled during the reaction and the (meth)acrylic anhydride formed is subsequently separated by distillation. However, the use of this process comes up against problems of polymerization during the distillation stage carried out directly from the reactor surmounted by a distillation column. In addition, the amount of (meth)acrylic anhydride produced is limited by the size of the reactor, all the more so as the reactants are introduced all at once into the reactor and as there is, for this reason, no optimization of the reaction capacity.

In order to overcome this problem, the proposal was made, in Application EP 1 273 565, to remove the acetic acid at least in part as it is formed and to at least partially replace the acetic acid removed by continuous introduction into the reaction medium, during the reaction, of acetic anhydride and/or (meth)acrylic acid. This process brings about a substantial improvement in the stabilization of the reaction medium without, however, completely solving the problem of formation of polymers in suspension, which makes it necessary to purify, by filtration, the crude $(M)AA_2O$ obtained after removal of the residual reactants and light byproducts. This filtration is problematic to carry out due to the highly lacrymatory nature of $(M)AA_2O$.

Patent Application US 2002/0161260 provides for the use of catalysts based on Cr, Zn, Cu, Ca, Zr, Li, La, Na or Hf in the form in particular of carboxylic acid salts. However, the use of these catalysts does not make it possible to obtain a significant increase in productive output with respect to the abovementioned processes.

The reaction scheme for transanhydrization between (meth)acrylic acid ((M)AA) and acetic anhydride ($Ac_2O$) to produce (meth)acrylic anhydride ($(M)AA_2O$) can be summarized as follows with the two main reactions:

Reaction 1: formation of acetic/(meth)acrylic mixed anhydride and acetic acid (AcOH)

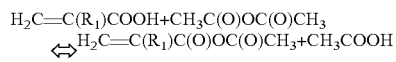

with $R_1$=H or $CH_3$.

Reaction 1 is very fast.
Reaction 2: reaction between the mixed anhydride and (M)AA

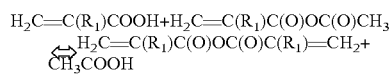

This synthesis is conventionally carried out under batchwise conditions in an installation such as that described in FIG. 1. The configuration for delayed addition of the reactants, such as described in document EP 1 273 565, is not represented in this figure. The reactants, (M)AA and $Ac_2O$, with at least one polymerization inhibitor, are introduced at 1 into the reactor R1 surmounted by a distillation column C1. The shifting of the equilibria is carried out by removing, by distillation at 2, the acetic acid as it is formed. The distillation column C1 acts both to remove the acetic acid generated in the reaction and to shift, for this reason, the reaction equilibria but also to distill, on conclusion of the reaction, the unconverted reactants, the light byproducts of mixed anhydride type and optionally the desired product $(M)AA_2O$. Generally, a distillation fraction $F_1$ composed of acetic acid, a fraction $F_2$ predominantly comprising acetic acid, (meth)acrylic acid and acetic/(meth)acrylic mixed anhydride, a fraction $F_3$ predominantly comprising acetic/(meth)acrylic mixed anhydride with a small amount of $(M)AA_2O$ and a fraction $F_4$ predominantly comprising the desired $(M)AA_2O$ are collected. The $(M)AA_2O$ can also be recovered directly in the reactor heel after distillation of the fractions $F_1$, $F_2$ and $F_3$. However, it is generally necessary to carry out a filtration of this reactor heel in order to obtain a correct quality of the product. The fractions $F_2$ and $F_3$ are for their part generally recycled all at once or continuously to the reaction (not represented in the figure).

The use of the existing processes comes up against problems, more or less marked, of fouling owing to the fact that the reaction is always carried out at high conversion of the reactants. The fact of extending the reaction time in order to achieve a high degree of conversion of the reactants is reflected by an increase in the content of heavy byproducts (Michael adducts type) and the formation of a large amount of (M)AA and $(M)AA_2O$ polymers, despite the presence of polymerization inhibitors, at the expense of the selectivity and of the cost of fouling of the reactor.

The fact of carrying out the distillation phase in the same equipment as the reaction further accentuates the phenomenon of production of polymers, which go into fine suspension in the crude reaction mixture. During the distillation phase, the gradual fall in the level of liquid in the reactor is reflected by prolonged contact of the unstabilized or relatively unstabilized monomers, which reflux from the column or which are condensed on contact with cold walls (this is the case, for example, when the dome of the reactor is insufficiently heat insulated). This contacting, by trickling, with the hot wall of the jacket of monomers which are unstabilized or relatively unstabilized is reflected by the formation of polymers which foul the reactor. When the $(M)AA_2O$ is recovered in the crude state, freed simply from the fractions $F_1/F_2/F_3$, it is necessary to filter this in order to remove the suspended polymers. This filtration is rendered problematic by the highly lacrymatory nature of $(M)AA_2O$, particularly during the cleaning of the filters. When $(M)AA_2O$ is recovered in the pure state by distillation, the reactor becomes completely fouled up.

Furthermore, the distillation column, generally well suited to the distillation of the acetic acid generated during the reaction, is not always the ideal compromise, both in capacity and in efficiency, for the distillation of the fractions $F_2/F_3/F_4$. In addition, the presence under hot conditions of the crude reaction product in the reactor throughout the duration of the distillation is very harmful for the reasons described above.

SUMMARY OF THE INVENTION

It is thus an aim of the present invention to overcome the various disadvantages mentioned above by providing an improved process for manufacture of (meth)acrylic anhydride which suppresses the problems of fouling of the reactor and which avoids the problematic operation of filtering the crude (M)AA$_2$O product, while resulting in a gain in terms of selectivity and of purity of the product obtained.

A subject matter of the invention is thus a process for the manufacture of (meth)acrylic anhydride by transanhydrization between (meth)acrylic acid and acetic anhydride in the presence of at least one polymerization inhibitor, characterized in that it comprises the following stages:
a) the reaction is carried out in a reactor R1 surmounted by a distillation column C1 until the reactants have been partially converted,
b) the crude reaction mixture resulting from stage a) is transferred into an intermediate storage vessel S1 which continuously feeds a second distillation column C2,
c) the (meth)acrylic anhydride is recovered at the bottom of column C2 and a fraction comprising essentially the unconverted reactants and the light byproducts is recovered at the column top,
d) the top fraction from column C2 is recycled in the reactor R1 all at once or continuously.

This process is characterized in that the crude reaction mixture, the conversion of the reactants of which is only partial, is continuously distilled and in that the operating phases, reaction and distillation, are separated into two distinct installations.

BRIEF DESCRIPTIONS OF THE DRAWINGS

Such a process makes possible an increase in the productive output which can reach around 50% in comparison with processes of the prior art.

Other characteristics and advantages of the invention will now be described in detail in the account which follows and with reference to FIG. 2, which represents a simplified operating diagram of the process of the invention.

DETAILED DESCRIPTION OF THE INVENTION

In the process according to the invention, the crude reaction product, the conversion of the reactants of which has deliberately not been driven to completion in order to limit the formation of heavy byproducts and of polymers and to achieve an increase in productive output, is transferred into an intermediate storage vessel. The crude reaction product is subsequently continuously distilled on a topping column particularly well suited to the removal of the residual reactants and light byproducts. The (M)AA$_2$O recovered at the bottom of this column has a purity of greater than 97% and is devoid of suspended polymers and, for this reason, does not have to be filtered.

Figure 1:
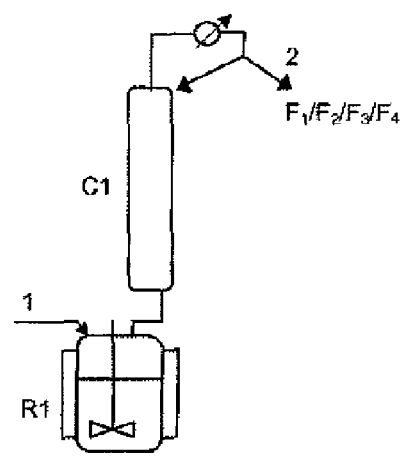
FIG. 1 shows a conventional batchwise equipment configuration for carrying out a transanhydrization reaction.
Figure 2:
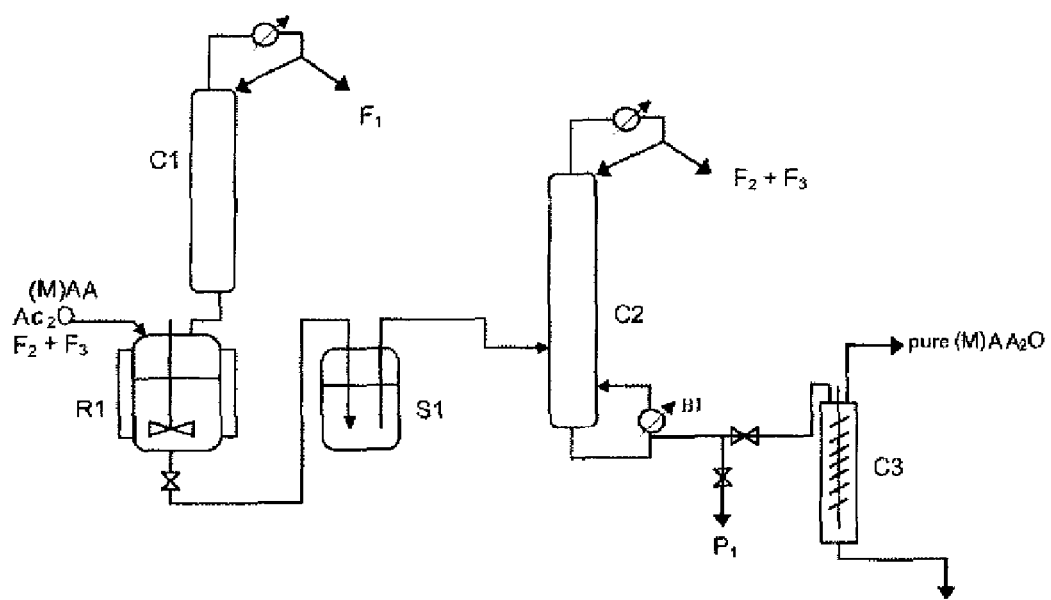
FIG. 2 shows a simplified operating diagram for carrying out a process in accordance with the present invention.

With reference to FIG. 2, the reactants (M)AA and Ac$_2$O are introduced into a reactor R1 surmounted by a distillation column C1 which is used to remove the acetic acid as it is formed. Preferably, methacrylic acid MAA is used. The reaction phase can be carried out batchwise, with introduction of a maximum charge allowed by the reactor. The molar ratio of the (M)AA to the Ac$_2$O is generally between 0.5 and 5, preferably between 1.8 and 2.2. The reaction phase can also be carried out batchwise with introduction of a starting charge followed by delayed addition of one or more reactant(s), continuously or batchwise, throughout the duration of the reaction, making it possible to occupy the space released by the removal of the acetic acid. The operating conditions of this preferred embodiment are described in detail in the document EP 1 273 565. In particular, the starting charge introduced into the reactor preferably exhibits a starting (M)AA/Ac$_2$O molar ratio of between 2.5 and 11, preferably between 9 and 11, the reactant added further advantageously being the Ac$_2$O and the overall (M)AA/Ac$_2$O molar ratio preferably being between 0.5 and 5, particularly between 1.8 and 2.2.

The reaction phase can also be carried out continuously with continuous withdrawal of the crude reaction product devoid of suspended solid, without it being necessary to filter it.

In the process according to the invention, the reaction is carried out until the reactants have been partially converted, that is to say until the content of (M)AA$_2$O in the crude reaction product has reached at most 75%, preferably until the content of (M)AA$_2$O in the crude reaction product is between 50% and 70%, preferably between 50% and 60%, the remainder being composed of (M)AA, Ac$_2$O and unconverted mixed anhydride.

Generally, the reaction is carried out for a period of time which can range from 6 to 8 h, which represents a period of time which is markedly shorter than that necessary for a more forceful conversion of the reactants. The reactor is thus released more rapidly in order to carry out a further synthesis and the result of this is that the productive output of the plant is increased.

The reaction temperature is generally between 50° C. and 120° C., advantageously between 85° C. and 105° C. The pressure is adjusted according to the reaction temperature chosen. Generally, it is between 20 and 200 mmHg (0.0267 and 0.2666 bar). The temperature of the regulating plate of the column (sensitive plate) is advantageously adjusted during the reaction according to the pressure, so as to correspond to the distillation temperature of the acetic acid. By operating in this way, a fraction F$_1$ is obtained at the top of column C1 with an acetic acid purity of greater than 90% which can even exceed 99%.

According to the invention, the reaction is carried out in the presence of at least one polymerization inhibitor introduced into the reactor and also into the distillation column.

Use may be made, as examples of polymerization inhibitors, of the compounds well known to a person skilled in the art, in particular hydroquinone, hydroquinone monomethyl ether, phenothiazine, di(tert-butyl)-para-cresol (BHT), 2,4-dimethyl-6-(tert-butyl)phenol (Topanol A), para-phenylenediamine, di(tert-butyl)catechol, 4-hydroxy-TEMPO (4-hydroxy-2,2,6,6-tetramethylpiperidine 1-oxyl) or TEMPO derivatives, taken alone or as a mixture, in a proportion of 100 to 5000 ppm with respect to the mixture of reactants.

According to a preferred embodiment of the invention, the reaction phase is carried out in the absence of catalysts. However, it is possible to carry out the reaction in the presence of a catalyst, such as sulfonic acids in the free form or attached to a polymeric support, which are described in the documents EP 196 520 and DE 102006029320, or the catalysts described in patent application US 2002/0161260. In the context of the present invention, where the conversion is not driven to completion, the use of these catalysts is not essential.

Bubbling of air or of air depleted to 8% in oxygen can be carried out throughout the reaction.

The crude product obtained on conclusion of the reaction phase is generally clear, devoid of polymers and freed from the acetic acid generated during the reaction.

According to stage b) of the process according to the invention, said crude reaction product is transferred into an intermediate storage vessel S1 when the desired degree of conversion of the reactants is reached. According to a specific embodiment of the invention, the reaction phase is carried out continuously and the crude reaction product is withdrawn continuously by modifying the operating conditions, in particular the reaction temperature and the reflux ratio of the column C1 allowing the removal of the acetic acid.

The storage vessel S1 is used to continuously feed a distillation column C2 particularly well suited to the removal of the residual reactants and light byproducts, such as the mixed anhydride formed by reaction of 1 mol of (M)AA with 1 mol of $Ac_2O$. The distillation column C2 preferably has a separation efficiency of greater than 10 theoretical plates, preferably greater than 15 theoretical plates. The packing of the column can be a conventional packing, random or structured, or a mixture of these two types of packing. The heating of the column can be provided by a forced circulation thermosiphon.

The feed rate of the column C2 can vary within wide limits and depends on the plant and on the size of the column.

A fraction $F_2+F_3$, comprising the unconverted reactants and the light byproducts, is recovered continuously at the top of column C2 and is intended to be recycled in the reactor R1 (stage d)), either directly and continuously or after storage and stabilization with one or more polymerization inhibitors. The fraction $F_2+F_3$ has been found, surprisingly, to exhibit good stability on storage, whereas, in the processes corresponding to the state of the art, the storage time before polymerization is relatively short, which implies destroying the fractions $F_2$ without being able to recycle them in the reactor. This constitutes an economic loss which is not exhibited in the context of the process according to the invention where, on the contrary, a saving in starting materials is observed.

The (meth)acrylic anhydride P1 is recovered at the bottom of column C2 with a purity of greater than 97% without requiring filtration, i.e. a greater purity than that generally obtained with the conventional processes (approximately 90-94%).

The $(M)AA_2O$ resulting from the process according to the invention can then be used directly as synthesis reactant, in particular for preparing, for example, dimethylaminopropyl (meth)acrylate by reaction with dimethylaminopropanol.

According to a specific embodiment of the invention, the process comprises an additional stage e) of purification of the $(M)AA_2O$ recovered at the bottom of column C2 using a device with a short residence time, such as a film evaporator, represented by the installation C3 in FIG. 2, in order to remove the heavy byproducts and polymerization inhibitors which may be present. The $(M)AA_2O$ thus purified has a purity of at least 99%, thus markedly greater than that which can be achieved with the conventional processes.

The present invention is illustrated by means of the following examples without, however, having a limiting nature.

EXAMPLES

The percentages are expressed therein by weight.
The following abbreviations are used:
$MAA_2O$: methacrylic anhydride
MAA: methacrylic acid
$Ac_2O$: acetic anhydride
AcOH: acetic acid
Mixed Anhydride: $H_2C=C(CH_3)C(O)OC(O)CH_3$
Topanol A: 2,4-dimethyl-6-(tert-butyl)phenol
BHT: 2,6-di(tert-butyl)-para-cresol

Example 1

Comparative 302 g of $Ac_2O$, 576 g of MAA, 0.64 g of Topanol A and 0.19 g of BHT are introduced into a jacketed glass reactor R1 with a working volume of 1 l which is stirred mechanically (4-bladed propeller mixer) and which is surmounted by a distillation column C1 of 15 theoretical plates with a condenser and a reflux head. Bubbling with depleted air is maintained in the reaction medium throughout the duration of the synthesis. The temperature of the reactor is kept between 90° C. and 95° C. during the reaction, the working pressure being gradually lowered from 150 mmHg to 50 mmHg.

On conclusion of this reaction phase, i.e. a period of time of 10 h, 478 g of a crude reaction product are obtained, which product comprises 70% of $MAA_2O$. During this stage, 375 g of AcOH are produced and removed by distillation as they are formed. The light products (fraction $F_2$: removal of $Ac_2O$; fraction $F_3$: removal of MAA and Mixed Anhydride) are subsequently distilled off while lowering the column top pressure to 15 mmHg and while allowing the temperature to advance up to 102° C. The amount of $F_2$ and $F_3$ obtained is 100 g. These fractions are combined and stabilized with 720 ppm of Topanol A in order to be recycled all at once to the following reaction. The $MAA_2O$ (300 g) is obtained by distillation of a fraction $F_4$. The mean composition of the fraction $F_4$ is 95.5% of $MAA_2O$, 2.5% of heavy compounds, 1% of MAA and 0.7% of Mixed Anhydride. At the end of the distillation, the reactor is highly fouled.

Example 2

Comparative

The same reaction is carried out as in example 1 except that the $MAA_2O$ (330 g) is obtained after the removal of the fractions $F_1$, $F_2$ and $F_3$ as a bottom product from the reactor R1, after emptying the reactor and filtering under pressure in order to remove the polymers. The mean composition is 94% of $MAA_2O$, 4% of heavy products, 1% of MAA and 0.7% of Mixed Anhydride.

Example 3

According to the Invention

The reactor used for the reaction phase and also the feeding with reactants and operating conditions are those described in example 1. After reacting for 6 h, the crude reaction product representing 676 g (composition: 60% of $MAA_2O$, 10% of MAA, 15% of $Ac_2O$, 11% of Mixed Anhydride, 1% of heavy products+stabilizers) is cooled and transferred without difficulty into a holding tank S1 for feeding a column C2 at the rate of 80 g/h at mid-column. No fouling of the reactor was observed.

The column C2 has a diameter of 30 mm and is equipped with stacked packing of Multiknit type. It exhibits a number of theoretical plates of 20. The heating is provided by a thermosiphon and the vacuum by a vane pump.

The 80 g/h of crude product are divided up as follows: 48.8 g/h at the column bottom and the remainder, representing the light products, at the column top. The top products are stored in a holding tank in order to be recycled to the following reaction. The condenser and the reflux are stabilized by a 5% solution of Topanol A in $MAA_2O$. Depleted air is injected into the reboiler. The working pressure is 15 mmHg at the column top and the bottom temperature is 91° C. The column bottom product thus obtained comprises $MAA_2O$ with a purity of 97.5%.

The synthesis of dimethylaminopropylamide from dimethylaminopropylamine and the grades of $MAA_2O$ obtained on conclusion of comparative examples 1 and 2 and of example 3 resulted in better purities with the grade of $MAA_2O$ obtained according to example 3 according to the invention.

What is claimed is:

1. A process for the manufacture of (meth)acrylic anhydride by transanhydrization between (meth)acrylic acid and acetic anhydride in the presence of at least one polymerization inhibitor, characterized in that it comprises the following stages:
   a) reacting, in a reactor R1 surmounted by a first distillation column C1, (meth)acrylic acid and acetic anhydride until the reactants have been partially converted to a crude reaction mixture,
   b) transferring the crude reaction mixture resulting from stage a) into an intermediate storage vessel S1 which continuously feeds a second distillation column C2,
   c) recovering (meth)acrylic anhydride at the bottom of second distillation column C2 and recovering a top fraction comprising essentially unconverted reactants and light byproducts at the second distillation column top, and
   d) recycling the top fraction from column C2 to reactor R1 all at once or continuously.

2. The process as claimed in claim 1, characterized in that the content of (meth)acrylic anhydride in the crude reaction mixture on conclusion of stage a) is at most equal to 75%.

3. The process as claimed in claim 1, characterized in that stage a) is carried out batchwise.

4. The process as claimed in claim 1, characterized in that stage a) is carried out batchwise with introduction of a starting charge of (meth)acrylic acid and acetic anhydride followed by delayed addition of one or more reactant(s), continuously or batchwise, throughout the duration of the reaction.

5. The process as claimed in claim 1, characterized in that stage a) and the transfer of the crude reaction mixture are carried out continuously.

6. The process as claimed in claim 1, characterized in that stage a) is carried out in the absence of catalysts.

7. The process as claimed in claim 1, additionally comprising a stage e) of purifying the (meth)acrylic anhydride recovered at the bottom of column C2 using a device with a short residence time.

8. The process as claimed in claim 1, characterized in that the content of (meth)acrylic anhydride in the crude reaction mixture on conclusion of stage a) is at between 50% and 70%.

* * * * *